United States Patent
Sholtis et al.

(10) Patent No.: US 8,041,580 B1
(45) Date of Patent: Oct. 18, 2011

(54) FORECASTING CONSEQUENCES OF HEALTHCARE UTILIZATION CHOICES

(75) Inventors: Steven Sholtis, El Dorado Hills, CA (US); Thomas Anthony Frasher, Sunnyvale, CA (US); Todd M. Fitch, Santa Clara, CA (US)

(73) Assignee: Intuit Inc., Mountain View, CA (US)

( * ) Notice: Subject to any disclaimer, the term of this patent is extended or adjusted under 35 U.S.C. 154(b) by 723 days.

(21) Appl. No.: 12/039,131

(22) Filed: Feb. 28, 2008

(51) Int. Cl.
*G06Q 50/00* (2006.01)
(52) U.S. Cl. .............................................. 705/2; 705/3
(58) Field of Classification Search .................. 705/2–4
See application file for complete search history.

(56) References Cited

U.S. PATENT DOCUMENTS

| | | | |
|---|---|---|---|
| 2002/0147617 A1* | 10/2002 | Schoenbaum et al. | 705/4 |
| 2003/0101076 A1* | 5/2003 | Zaleski | 705/2 |
| 2003/0135392 A1* | 7/2003 | Vrijens et al. | 705/2 |
| 2004/0064341 A1* | 4/2004 | Langan et al. | 705/2 |
| 2006/0282244 A1* | 12/2006 | Chotai et al. | 703/11 |
| 2007/0244714 A1* | 10/2007 | McCluskey et al. | 705/2 |
| 2008/0091463 A1* | 4/2008 | Shakamuri | 705/2 |

* cited by examiner

*Primary Examiner* — Gerald J. O'Connor
*Assistant Examiner* — Sind Phongsvirajati
(74) *Attorney, Agent, or Firm* — Gunnison, McKay & Hodgson, L.L.P.; Philip McKay

(57) ABSTRACT

A computer system implemented method and process for forecasting the consequences of healthcare utilization choices whereby health data associated with a user is obtained and analyzed to determine disease risk factors. Any determined disease risk factors present in the healthcare data are then used to generate a healthcare utilization consequences report based on various user actions/inactions. The healthcare utilization consequences report can include healthcare recommendations, economic information, actuarial information and comparisons between implementing/not implementing the healthcare recommendations.

25 Claims, 3 Drawing Sheets

FORECASTING CONSEQUENCES OF HEALTHCARE UTILIZATION CHOICES

BACKGROUND

Typically, healthcare insurance provides coverage for both current maladies as well as preventative healthcare to mitigate future healthcare issues for which individuals may be predisposed. Predisposition to disease may be due to a variety of risk factors such as genetics, lifestyles, behaviors and/or environmental influences. Unfortunately, healthcare insurance is expensive and not everyone can afford to obtain coverage. However, for many individuals obtaining healthcare insurance is a matter of choice and some of these individuals are not inclined to incur the expense for what they may consider an intangible benefit.

For example, there is a strong temptation to forgo healthcare insurance among young adults who typically do not suffer from any serious maladies in order to maximize current disposable income. As a result, these individuals will also be more likely to defer or forego obtaining necessary preventative healthcare, as the entire expense of obtaining the preventative healthcare is perceived as an "optional" expense rather than an investment in their future health and wellbeing.

Unfortunately, the decision by these individuals to forego obtaining healthcare insurance, and thus often also foregoing recommended preventative healthcare, is typically made without full awareness and/or careful consideration of the future economic, personal, and/or family consequences resulting from the lack of receiving the recommended preventive healthcare.

As noted above, one reason for this "impromptu" decision-making is that the perceived benefit seems remote, in terms of both time and probability. In addition, the difficulty in obtaining, interpreting and comparing each individual's personal health history with statistical measures associated with those of the general population further complicates the situation. Consequently, there currently is no simple mechanism to consolidate, analyze and output the results in an easily understandable format so that these individuals can see the projected tangible results of their choices so they can make an informed decision regarding their healthcare insurance and/or utilization of preventative healthcare.

As a result of the above situation, many individuals defer obtaining, or otherwise fail to obtain, recommended preventative healthcare early on in life because they are never given the tools to properly analyze the situation. Consequently, many of these individuals will experience higher overall healthcare costs, reduced quality of life/disability, and/or reduced longevity.

SUMMARY

In accordance with one embodiment, a method and system for forecasting the consequences of healthcare utilization choices includes a process for forecasting the consequences of healthcare utilization choices whereby, in one embodiment, data representing personal and/or family health information associated with a user is obtained. In one embodiment, data representing personal and/or family health information associated with a user is analyzed by the process for forecasting the consequences of healthcare utilization choices to generate a personalized disease predisposition profile for the user. In one embodiment, using the personalized disease predisposition profile for the user, a healthcare utilization analysis is performed by the process for forecasting the consequences of healthcare utilization choices based on one or more healthcare utilization models. In one embodiment, a healthcare utilization consequences report is then generated by the process for forecasting the consequences of healthcare utilization choices. In one embodiment, the healthcare utilization consequences report is provided to the user for review and/or use in making healthcare, behavioral and/or lifestyle choices. In one embodiment, the healthcare utilization consequences report is provided to one or more healthcare providers for use in providing marketing offers targeted to the user based on the healthcare utilization consequences report.

In one embodiment, the data representing personal and/or family health information associated with a user includes, but is not limited to: data representing information related to any historical and/or present user illnesses; data representing information related to any historical and/or present user injuries; data representing information related to any historical and/or present preventative healthcare received by the user; data representing information related to any historical and/or present medications taken by the user; data representing information related to any historical and/or present illness associated with the user's family and/or the user's family health history; data representing information related to any historical and/or present user residences; data representing information related to any historical and/or present user occupations; data representing information related to any historical and/or present user environmental exposures that could affect the user's predisposition to a particular type of disease; and/or data representing any other information related to the user's historical state of health, current state of health, or that is determined of value in projecting the user's future state of health.

In one embodiment, at least part of the data representing personal and/or family health information associated with a user is obtained by the process for forecasting the consequences of healthcare utilization choices from the user's personal health record, in either a digital format and/or by scanning all or part of a user's printed health record into a computing system associated with the process for forecasting the consequences of healthcare utilization choices. In one embodiment, at least part of the data representing personal and/or family health information associated with a user is obtained by the process for forecasting the consequences of healthcare utilization choices from a computing system implemented data management system, such as a computing system implemented healthcare management system.

In one embodiment, at least part of the data representing personal and/or family health information associated with a user is obtained by the process for forecasting the consequences of healthcare utilization choices from one or more healthcare providers. In one embodiment, at least part of the data representing personal and/or family health information associated with a user is obtained by the process for forecasting the consequences of healthcare utilization choices from one or more healthcare insurance providers. In one embodiment, at least part of the data representing personal and/or family health information associated with a user is obtained by the process for forecasting the consequences of healthcare utilization choices from user input using a user interface and a user interface device.

In one embodiment, at least part of the data representing personal and/or family health information associated with a user is obtained by the process for forecasting the consequences of healthcare utilization choices from any combination of the above sources and/or from any source of the data representing personal and/or family health information associated with a user, such as those described herein, known in the relevant art at the time of filing, or as developed thereafter.

In one embodiment, the data representing personal and/or family health information associated with a user is analyzed by the process for forecasting the consequences of healthcare utilization choices to generate a personalized disease predisposition profile for the user that includes, but is not limited to, identified diseases the user may have or be prone to acquiring in the future due to genetic, lifestyle, behavior and/or environmental risk factors.

In one embodiment, using the personalized disease predisposition profile for a user, the healthcare utilization analysis is performed by the process for forecasting the consequences of healthcare utilization choices based on the user receiving little or no healthcare and/or not obtaining healthcare insurance. In one embodiment, using the personalized disease predisposition profile for a user, a healthcare utilization analysis is performed by the process for forecasting the consequences of healthcare utilization choices based on the user receiving generally recommended healthcare and/or obtaining healthcare insurance.

In one embodiment, using the personalized disease predisposition profile for a user, a healthcare utilization analysis is performed by process for forecasting the consequences of healthcare utilization choices based on the user making lifestyle choices and/or behavior modifications suggested to the user based on the personalized disease predisposition profile for the user. In one embodiment, using the personalized disease predisposition profile for the user, a healthcare utilization analysis is performed by process for forecasting the consequences of healthcare utilization choices based on the user not making lifestyle choices and/or behavior modifications suggested to the user based on the personalized disease predisposition profile for the user.

In one embodiment, using the personalized disease predisposition profile for a user, the healthcare utilization analysis is performed by the process for forecasting the consequences of healthcare utilization choices and the forecasted outcomes of various choices on the part of the user in terms of projected future healthcare costs using actuarial data and demographic data. In one embodiment, using the personalized disease predisposition profile for a user, the healthcare utilization analysis is performed by process for forecasting the consequences of healthcare utilization choices, and the forecasted outcomes of various choices on the part of the user in terms of projected longevity based at least in part, on all, or part of the actuarial and demographic data.

In one embodiment, using the personalized disease predisposition profile for a user, the healthcare utilization analysis is performed by process for forecasting the consequences of healthcare utilization choices in which the forecasted outcomes of various choices on the part of the user is projected in terms of quality of life/disability based at least in part, on all, or part of the actuarial data and demographic data.

In one embodiment, at least part of the results of the healthcare utilization analysis performed by the process for forecasting the consequences of healthcare utilization choices are collected in a healthcare utilization consequences report generated by the process for forecasting the consequences of healthcare utilization choices. In one embodiment, the healthcare utilization consequences report shows the comparative healthcare costs of one or more choices on the part of the user in terms of projected future healthcare costs. In one embodiment, the healthcare utilization consequences report shows comparative healthcare costs of one or more choices on the part of the user in terms of projected longevity. In one embodiment, the healthcare utilization consequences report shows comparative healthcare costs of one or more choices on the part of the user in terms of projected quality of life/disability.

In one embodiment, the healthcare utilization consequences report is provided to a user via a computing system, such as those described herein, known in the relevant art at the time of filing, or as developed thereafter. In one embodiment, the healthcare utilization consequences report is provided to a user via a computing system implemented data management system, such as those described herein, known in the relevant art at the time of filing, or as developed thereafter.

In one embodiment, the healthcare utilization consequences report is provided to a user via a network, such as those described herein, known in the relevant art at the time of filing, or as developed thereafter. In one embodiment, the healthcare utilization consequences report is provided to a user via a mechanism for transferring and/or relating information, such as those described herein, known in the relevant art at the time of filing, or as developed thereafter.

In one embodiment, the healthcare utilization consequences report is provided to one or more healthcare providers for use in providing marketing offers targeted to the user based on the healthcare utilization consequences report.

Figure 1:
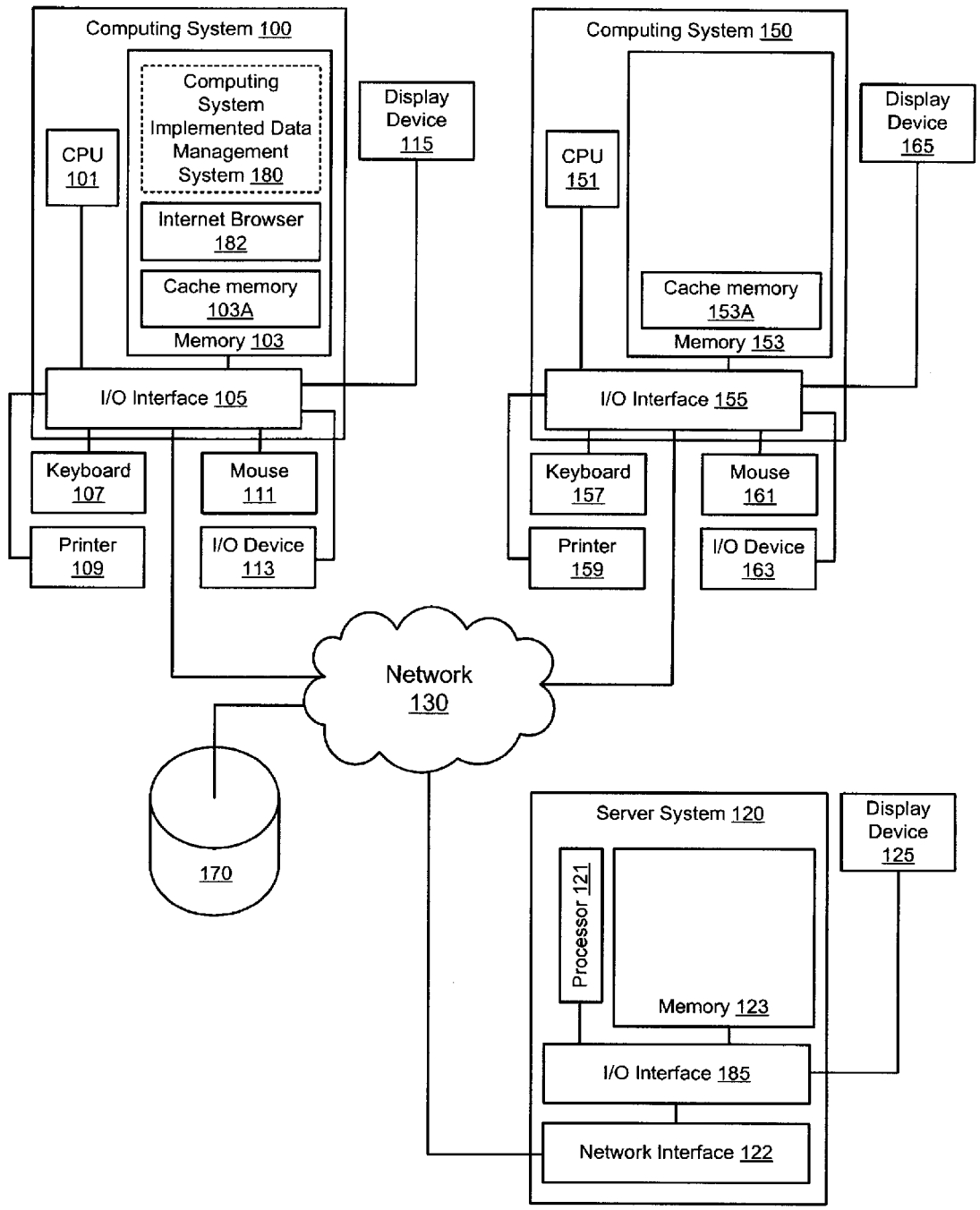
FIG. 1 is a block diagram of an exemplary hardware architecture for implementing one embodiment.

Common reference numerals are used throughout the figures and the detailed description to indicate like elements. One having ordinary skill in the art will appreciate that the above figures are examples and that other architectures, modes of operation, orders of operation and elements/functions can be provided and implemented without departing from the characteristics and features of the various embodiments, as set forth in the claims.

DETAILED DESCRIPTION

Embodiments will now be discussed with reference to the accompanying figures, which show one or more exemplary embodiments. Embodiments may be presented in many different forms and should not be construed as limited to the exemplary embodiments set forth herein, shown in the figures and/or described below. Rather, these exemplary embodiments are provided to allow a complete disclosure that conveys the principles of the various embodiments, as set forth in the claims, to those of ordinary skill in the art.

In accordance with one embodiment, a method and system for forecasting the consequences of healthcare utilization choices includes a process for forecasting the consequences of healthcare utilization choices whereby, in one embodiment, the data representing personal and/or family health information associated with a user is obtained. In one embodiment, the data representing personal and/or family health information associated with a user is analyzed by a process for forecasting the consequences of healthcare utilization choices to generate a personalized disease predisposition profile for a user. In one embodiment, using the personalized disease predisposition profile for a user, a healthcare utilization analysis is performed by the process for forecasting the consequences of healthcare utilization choices based on one or more healthcare utilization models.

In one embodiment, a healthcare utilization consequences report is then generated by process for forecasting the consequences of healthcare utilization choices. In one embodiment, the healthcare utilization consequences report is provided to a user for review and/or for use in making healthcare, behavioral and/or lifestyle choices. In one embodiment, the healthcare utilization consequences report is provided to one or more healthcare providers for use in providing marketing offers targeted to the user based on the healthcare utilization consequences report.

Hardware System Architecture

FIG. 1 is a block diagram of an exemplary hardware architecture for implementing one embodiment of a system and method for forecasting the consequences of healthcare utilization choices, such as exemplary processes 200 and/or 300 (FIGS. 2,3) discussed herein, that includes: a computing system 100, e.g., a first computing system; a computing system 150, e.g., a second computing system; a server system 120; and a database 170, all operatively coupled by a network 130.

As shown in FIG. 1, computing system 100 typically includes a central processing unit (CPU) 101, an input/output (I/O) interface 105, and a memory system 103, including a cache memory 103A. In one embodiment, memory system 103 includes all, or part of, a computing system implemented data management system 180 such as, but not limited to: a computing system implemented healthcare management system; a computing system implemented personal and/or business financial management system; a computing system implemented personal and/or healthcare management system; a computing system implemented personal and/or business accounting system; a computing system implemented point of sale system; a computing system implemented personal and/or business tax preparation system; and/or any other computing system implemented data management system, such as those described herein, known in the relevant art at the time of filing, or as developed thereafter.

In one embodiment, computing system implemented data management system 180 is stored, in whole, or in part, in memory system 103, and is used by, or includes, a process for forecasting the consequences of healthcare utilization choices, such as exemplary processes 200 and/or 300 (FIGS. 2,3), as discussed below.

Returning to FIG. 1, computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device and/or computer program product, as described herein, capable of inputting data to, and outputting data from, computing system 100, such as those described herein, known in the relevant art at the time of filing, or as developed thereafter. As discussed in more detail below, in one embodiment, a process for forecasting the consequences of healthcare utilization choices 200 and/or 300 (FIGS. 2,3) and/or a computing system implemented data management system 180 (FIG. 1) is/are operatively installed, in whole, or in part, into computing system 100 via I/O device 113, such as from a CD, DVD, floppy disk, portable hard drive, memory stick, download site, or other medium and/or computer program product as described herein. In one embodiment, computing system 100 also includes an Internet browser 182 and/or access capability that, in one embodiment, is stored, in whole, or in part in memory 103.

In one embodiment, computing system 100 is a computing system accessible by another computing system, such as computing system 150 (discussed below), that includes components that can execute all, or part, of process for forecasting the consequences of healthcare utilization choices 200 and/or 300 (FIGS. 2,3), and/or computing system implemented data management system 180 (FIG. 1), in accordance with at least one of the embodiments as described herein.

Analogously, computing system 150 typically includes a CPU 151, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, such as those described herein, known in the relevant art at the time of filing, or as developed thereafter. In one embodiment, computing system 150 is accessible by a provider of process for forecasting the consequences of healthcare utilization choices 200 and/or 300 (FIGS. 2,3), and/or computing system implemented data management system 180 (FIG. 1), and, in one embodiment, memory system 153 includes all, or part of, the data representing personal and/or family health information associated with a user, as is discussed in more detail below.

In one embodiment, all, or part of, process for forecasting the consequences of healthcare utilization choices 200 and/or 300 (FIGS. 2,3), and/or computing system implemented data management system 180 (FIG. 1), can also be operatively installed, in whole, or in part, into computing system 150 from computing system 100 for storage in memory system 153 and/or cache memory 153A.

Also shown in FIG. 1 is an exemplary database 170. In one embodiment, database 170 is a data storage device, a designated server system or computing system, or a designated portion of one or more server systems or computing systems, such as computing systems 100, 150 and/or server system 120, or a distributed database, and/or a hard drive. In one embodiment, database 170 is a dedicated mass storage device implemented in software, hardware, or a combination of hardware and software. In one embodiment, database 170 is a web-based resource. As discussed in more detail below, in one embodiment, database 170 is under the control of the user, and/or the user's agents, and/or a provider of process for forecasting the consequences of healthcare utilization choices 200 and/or 300 (FIGS. 2,3), and/or a computing system implemented data management system, such as a computing system implemented data management system 180 (FIG. 1).

In one embodiment, database 170 is used, controlled, and/or accessible by, a provider of and/or a system and process for forecasting the consequences of healthcare utilization choices, such as process for forecasting the consequences of healthcare utilization choices 200 and/or 300 (FIGS. 2,3), and all, or part, of the data representing personal and/or family health information associated with a user is stored in database 170, typically in an account associated with a user.

In one embodiment, database 170 is used, controlled, and/or accessible by, a provider of and/or a computing system implemented data management system, such as a computing system implemented data management system 180, and all, or part, of the data representing personal and/or family health information associated with a user is stored in database 170, typically in accounts associated with one or more users. In one embodiment, database 170 is used, controlled, and/or accessible by one or more healthcare providers.

In one embodiment, computing systems 100 and 150, and database 170, are coupled to a server system 120 through network 130. In one embodiment, server system 120 typically includes a server system display device 125, a server system processor 121, a server system memory 123, a server system input/output (I/O) interface 185 and a server system network interface 122.

In one embodiment, server system 120 is used in a station-to-station arrangement, such as a peer-to-peer, or hybrid peer-to-peer arrangement, as an indexing and/or central server used to connect a first computing system, such as computing system 100, and a second computing system, such as computing system 150.

In one embodiment, server system 120 is used, controlled, and/or accessible by, a provider of and/or a system and process for forecasting the consequences of healthcare utilization choices, such as process for forecasting the consequences of healthcare utilization choices 200 and/or 300 (FIGS. 2,3), and all, or part, of the data representing personal and/or family health information associated with a user is stored in server system 120 (FIG. 1), typically in accounts associated with one or more users. In one embodiment, server system 120 is used, controlled, and/or accessible by, a provider of and/or a computing system implemented data management system, such as a computing system implemented data management system 180, and all, or part of, the data representing personal and/or family health information associated with a user is stored in server system 120, typically in accounts associated with one or more users. In one embodiment, server system 120 is used, controlled, and/or accessible by one or more healthcare providers.

Network 130 can be any network or network system that is of interest to a user such as, a peer-to-peer network, a hybrid peer-to-peer network, a Local Area Network (LAN), a Wide Area Network (WAN), a public network, such as the Internet, a publicly switched telephone network (PSTN), a private network, a combination of different network types, or other wireless, optical, wired, and/or a wireless and wired combination network capable of allowing communication between two or more computing systems, such as those described herein, known in the relevant art at the time of filing, or as developed thereafter.

In various embodiments, server system 120 and I/O interface 105 include analog modems, digital modems, a network interface card, a broadband connection, or any other means of communicably coupling computer systems 100 and 150, database 170, and server system 120 via network 130, such as those described herein, known in the relevant art at the time of filing, or as developed thereafter. Those of ordinary skill in the art will appreciate that the components shown in FIG. 1, such as computing systems 100 and 150, database 170, server system 120, and their respective components, are shown for illustrative purposes only and that architectures with more or fewer units can implement, and benefit from, the various exemplary embodiments.

Moreover, one or more components of computing system 100, computing system 150, database 170, and server system 120 may be located remotely from their respective system and accessed via a network, as discussed herein. In addition, the particular type of, and configuration of, computing systems 100 and 150, database 170, and server system 120 are not relevant.

As discussed in more detail below, in one embodiment, a process for forecasting the consequences of healthcare utilization choices, such as process for forecasting the consequences of healthcare utilization choices 200 and/or 300 (FIGS. 2,3), and/or a computing system implemented data management system, such as a computing system implemented data management system 180 (FIG. 1), and/or the data representing personal and/or family health information associated with a user is stored, in whole, or in part, in memory system 103 and/or cache memory 103A, of computing system 100, and/or memory system 153 and/or cache memory 153A of computing system 150, and/or in server memory system 123 of server system 120 and/or in database 170 and executed on a computing system, such as computing system 100 and/or computing system 150. As used herein, a memory refers to a volatile memory, a non-volatile memory, or any combination of the two.

Although a process for forecasting the consequences of healthcare utilization choices, such as process for forecasting the consequences of healthcare utilization choices 200 and/or 300 (FIGS. 2,3), and/or a computing system implemented data management system, such as computing system implemented data management system 180 (FIG. 1), are sometimes referred to herein, alternatively, as a process, a script, a routine, an application, a module, a program, a package, a component of a software system, a component of a software package, a component of a parent system, a plug-in, an applet, an operation and/or a feature of a parent system, this terminology is illustrative only.

In some embodiments, a process for forecasting the consequences of healthcare utilization choices, such as process for forecasting the consequences of healthcare utilization choices 200 and/or 300 (FIGS. 2,3), and/or a computing system implemented data management system, such as a computing system implemented data management system 180 (FIG. 1), are capable of being called by a process, a script, a routine, an application, a module, a program, a package, a component of a software system, a component of a software package, a component of a parent system, a plug-in, an applet, an operation and/or a feature of a parent system; and/or by an operating system, a runtime environment of one or more computing systems 100, 150 and/or server system 120.

In one embodiment, a process, a script, a routine, an application, a module, a program, a component of a software system, a package, a component of a software package, a component of a parent system, a plug-in, an applet, and/or operation is generally defined to be any executable or interpretable code. Moreover, those of ordinary skill in the art will appreciate that when it is said that a process, a script, a routine, an application, a module, a program, a component of a software system, a component of a software package, a component of a parent system, a plug-in, an applet, and/or operation takes some action, the action is the result of executing one or more instructions by a processor, such as CPUs 101 and 151, or server system processor 121. In one embodiment, execution of a process by CPU 101, CPU 151, or server system processor 121, results in the operations of an agent computer process (not shown) and/or a rule computer process (not shown).

In one embodiment, a process for forecasting the consequences of healthcare utilization choices, such as process for forecasting the consequences of healthcare utilization choices 200 and/or 300 (FIGS. 2,3), and/or a computing system implemented data management system, such as a computing system implemented data management system 180 (FIG. 1), and/or the data representing personal and/or family health information associated with a user, is/are provided in full, or in part, in, or on, a computer program product. Herein, a computer program product comprises a tangible medium and/or I/O device configured to store and/or transport computer readable code, such as those described herein, known in the relevant art at the time of filing, or as developed thereafter.

Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable code, such as those described herein, known in the relevant art at the time of filing, or as developed thereafter.

This computer readable medium may belong to a computing system, such as computing systems 100 and 150 of FIG. 1, described above. However, in some embodiments, the computer readable medium also may be removable and/or remotely accessible from one or more computing systems, such as computing systems 100 and/or 150 of FIG. 1.

For example, all, or part, of a process for forecasting the consequences of healthcare utilization choices, such as process for forecasting the consequences of healthcare utilization choices 200 and/or 300 (FIGS. 2,3), and/or a computing system implemented data management system, such as a computing system implemented data management system 180 (FIG. 1), and/or the data representing personal and/or family health information associated with a user, may be stored in a memory that is physically located in a separate location, such as server system memory 123, or database 170, of FIG. 1, which is different from a computing system, such as computing systems 100 and/or 150 of FIG. 1, in which a user is located as is discussed below.

In one embodiment, all, or part, of process for forecasting the consequences of healthcare utilization choices 200 and/or 300 (FIGS. 2,3), and/or a computing system implemented data management system 180 (FIG. 1), may be stored in a memory that is physically located, separate from the computing system's processor(s), such as CPUs 101 and 151 of FIG. 1, and the computing system CPUs can be coupled to the memory in a client-server system, such as server system 120 of FIG. 1, or, alternatively, via connection to another computing system, such as computing systems 100 and 150 of FIG. 1, via modems and analog lines, digital interfaces and a digital carrier line, or wireless or cellular connections, such as those described herein, known in the relevant art at the time of filing, or as developed thereafter.

Process

Herein, the terms "user", "healthcare consumer", "patient" and/or "customer" can be used interchangeably to denote a person or an agent of a person who interfaces with and/or otherwise interacts with a process for forecasting the consequences of healthcare utilization choices.

Herein, the term "healthcare provider" denotes any individual person, persons, agencies, institutions, organizations, businesses, and/or other entities that provide medical treatment, medications, therapy, advice, and/or equipment. For example, herein, the term "healthcare provider" includes, but is not limited to: healthcare insurance providers; healthcare plan administrators; doctors; nurses; technicians; therapists; pharmacists; dentists; hygienists; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "healthcare" includes any general and/or specialized treatment, assessment, insurance, maintenance, therapy, medication, exercise and/or diet advice, and/or other advice relating to all, or any portion of, a consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; recommended activity level changes; other lifestyle and/or behavioral changes; and/or surgical procedures; and/or any prescribed and/or suggested regime, medication, treatment, activity, avoided activity, and/or program designed to improve, maintain, and/or slow the degradation of, a healthcare consumer's state of health.

Herein, the term "computing system implemented data management system" includes, but is not limited to: computing system implemented personal and/or business healthcare management systems, computing system implemented personal and/or business financial management systems, computing system implemented personal and/or business tax preparation systems, computing system implemented personal and/or business accounting and/or invoicing systems, computing system implemented point of sale management systems, various other personal and/or business electronic data management systems, and/or processes, scripts, routines, applications, modules, programs, packages, components of a software system, components of a software package, components of a parent system, plug-ins, applets, operations and/or features of a parent system associated with one or more of the aforementioned computing system implemented data management systems, and/or other computing system implemented data management systems described herein, known in the relevant art at the time of filing, or as developed thereafter.

As used herein, the term "computing system," denotes, but is not limited to: a portable computer; a workstation; a two-way pager; a cellular telephone; a smart phone; a digital wireless telephone; a Personal Digital Assistant (PDA); a media player, i.e., an MP3 Player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "network" is used to denote any network or network system that is of interest such as, a peer-to-peer network, a hybrid peer-to-peer network, a Local Area Network (LAN), a Wide Area Network (WAN), a public network, such as the Internet, a private network, a publicly switched telephone network (PSTN), a combination of different network types, or other wireless, wired, and/or a wireless and wired combination network capable of allowing communication between two or more computing systems, such as those described herein, known in the relevant art at the time of filing, or as developed thereafter.

As used herein, the term "database" is used to define any data storage mechanism described herein, known at the time of filing or as developed thereafter, such as, but not limited to: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based resource. Herein, the term "database" can refer to a data storage means that is part of, or under the control of, any computing system, such as those described herein, known in the relevant art at the time of filing, or as developed thereafter.

Figure 2:
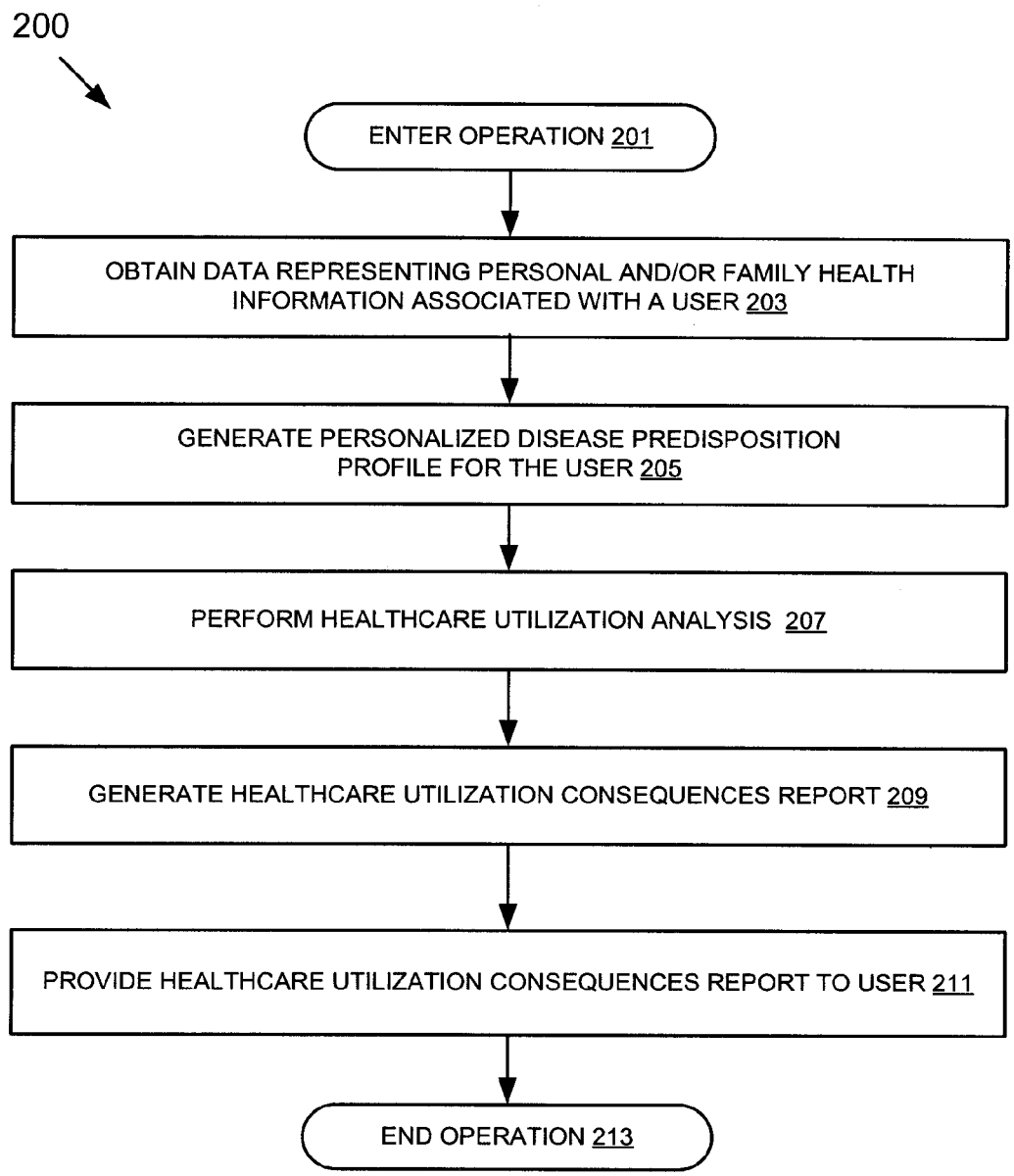
FIG. 2 is a flow chart for implementing a process for forecasting the consequences of healthcare utilization choices in accordance with one embodiment.

FIG. 2 is a flow chart depicting a process for forecasting the consequences of healthcare utilization choices 200 in accordance with one embodiment. Process for forecasting the consequences of healthcare utilization choices 200 begins at ENTER OPERATION 201 of FIG. 2 and flow proceeds to OBTAIN DATA REPRESENTING PERSONAL AND/OR FAMILY HEALTH INFORMATION ASSOCIATED WITH A USER OPERATION 203. In one embodiment, at OBTAIN DATA REPRESENTING PERSONAL AND/OR FAMILY HEALTH INFORMATION ASSOCIATED WITH A USER OPERATION 203, process for forecasting the consequences of healthcare utilization choices 200 obtains the data representing personal and/or family health information associated with a user.

In one embodiment, the data representing personal and/or family health information includes a variety of data as is described below. In one embodiment, the data representing personal and/or family health information associated with a user of OBTAIN DATA REPRESENTING PERSONAL AND/OR FAMILY HEALTH INFORMATION ASSOCIATED WITH A USER OPERATION 203 includes a health data component. In one embodiment, the health data component of the data representing personal and/or family health information associated with a user includes, but is not limited to, any historical and/or present: user illnesses; user injuries; user surgeries; user's actual healthcare utilization; healthcare insurance coverage utilized by the user; medications taken by the user; familial genetic disorders; compliance with recommended healthcare routines, regimens, programs and medications; environmental exposures that could affect a user's predisposition to a particular type of disease; and/or other health information about a user and/or a user's family that is deemed relevant and/or indicative of a user's future state of health.

In one embodiment, the data representing personal and/or family health information associated with a user of OBTAIN DATA REPRESENTING PERSONAL AND/OR FAMILY HEALTH INFORMATION ASSOCIATED WITH A USER OPERATION 203 includes a demographic data component. In one embodiment, the demographic data component of the data representing personal and/or family health information associated with a user includes, but is not limited to: any historical and/or present residences, occupations and/or military service of a user; user's age; user's gender; user's ethnicity; number of user children; number of user siblings; user's socioeconomic status; and/or any other demographic information about a user and/or a user's family deemed to be relevant and/or indicative of a user's future state of health.

In one embodiment, the data representing personal and/or family health information associated with a user of OBTAIN DATA REPRESENTING PERSONAL AND/OR FAMILY HEALTH INFORMATION ASSOCIATED WITH A USER OPERATION 203 includes a personal data component. In one embodiment, the personal data component of the data representing personal and/or family health information associated with a user includes, but is not limited to, any historical and/or present: risky lifestyles (e.g., illicit drug use, promiscuity, smoking, excessive alcohol consumption) of the user; relevant life events (e.g., divorce, death of loved ones, traumatic experiences, changes in employment, financial problems) of the user; risky endeavors (e.g., rock climbing, auto racing, sky diving, bungee jumping, travel to war torn countries and/or countries with high incidence rates of pathogenic diseases); behavioral and/or any other personal information about a user and/or a user's family that is deemed relevant and/or indicative of a user's future state of health.

In one embodiment, the data representing personal and/or family health information associated with a user of OBTAIN DATA REPRESENTING PERSONAL AND/OR FAMILY HEALTH INFORMATION ASSOCIATED WITH A USER OPERATION 203 includes an actuarial data component. In one embodiment, the actuarial data component of the data representing personal and/or family health information associated with a user includes, but is not limited to: data representing statistical risk estimates of a user's generational cohort group; healthcare economic costs for preventing and/or treating disease conditions at various stages of progression, quality of life/disability costs based on deferral or avoidance of recommended healthcare; healthcare recommendations to avoid and/or mitigate the onset of diseases based on disease predispositions; longevity information relevant to a user's generational cohort group; and/or any other actuarial information about the user and/or a user's family that is deemed relevant and/or indicative of a user's future state of health. In one embodiment, the data representing the actuarial information discussed above is obtained from third party government, academic, healthcare research and/or proprietary databases; a few examples of which include the U.S. Center for Disease Control (CDC), at URL WWW.CDC.GOV WebMD at URL WWW.WEBMD.COM, John Hopkins University at URL WWW.HOPKINSMEDICINE.ORG and National Institutes for Health at URL WWW.NIH.GOV.

In one embodiment, the data representing personal and/or family health information associated with a user of OBTAIN DATA REPRESENTING PERSONAL AND/OR FAMILY HEALTH INFORMATION ASSOCIATED WITH A USER OPERATION 203 is in the form of electronic data that is stored, in whole, or in part, in a database maintained by, accessible by, controlled by, owned by, or otherwise related to, a provider of process for forecasting the consequences of healthcare utilization choices 200 of FIG. 2 by any of the numerous mechanisms described herein, known in the relevant art at the time of filing, or as developed thereafter.

For example, in one embodiment, the data representing personal and/or family health information associated with a user of OBTAIN DATA REPRESENTING PERSONAL AND/OR FAMILY HEALTH INFORMATION ASSOCIATED WITH A USER OPERATION 203, is stored, in whole, or in part, in a memory system, such as memory system 103 and/or 153 or server memory system 123, or database 170, of FIG. 1, or in a cache memory, such as cache memory 103A and/or 153A of FIG. 1, or in any main memory or mass memory, associated with a computing device, such as computing system 100 and/or 150 described above.

Returning to FIG. 2, in one embodiment, the data representing personal and/or family health information associated with a user of OBTAIN DATA REPRESENTING PERSONAL AND/OR FAMILY HEALTH INFORMATION ASSOCIATED WITH A USER OPERATION 203 is stored, in whole, or in part, in any computing device and/or server system, such as computing system 100 (FIG. 1) or server system 120, or other device, in another location, or on/in a computer readable medium, and/or any other computer program product, as described herein. In one embodiment, the data representing personal and/or family health information associated with a user is stored, in whole, or in part, on and/or accessible from a webpage, in a web-based resource or available using a public network such as the Internet.

Returning to FIG. 2, in some embodiments, the data representing personal and/or family health information associated with a user of OBTAIN DATA REPRESENTING PERSONAL AND/OR FAMILY HEALTH INFORMATION ASSOCIATED WITH A USER OPERATION 203, stored as described above, is maintained, in whole, or in part, by the provider of process for forecasting the consequences of healthcare utilization choices 200. In these embodiments, access to the data representing personal and/or family health information associated with a user is then granted to process for forecasting the consequences of healthcare utilization choices 200 by providing access to the data representing personal and/or family health information associated with a user and/or providing the data representing personal and/or family health information associated with a user on a computer program product.

In some embodiments, the data representing personal and/or family health information associated with a user is obtained at OBTAIN DATA REPRESENTING PERSONAL AND/OR FAMILY HEALTH INFORMATION ASSOCIATED WITH A USER OPERATION 203 through a network of computing systems and/or server systems. In some embodiments, the data representing personal and/or family health information associated with a user is obtained/accessed/collected at OBTAIN DATA REPRESENTING PERSONAL AND/OR FAMILY HEALTH INFORMATION ASSOCIATED WITH A USER OPERATION 203 through e-mail, facsimile or through text messaging. In some embodiments, the data representing personal and/or family health information associated with a user is provided to process for forecasting the consequences of healthcare utilization choices 200 at OBTAIN DATA REPRESENTING PERSONAL AND/OR FAMILY HEALTH INFORMATION ASSOCIATED WITH A USER OPERATION 203 through any method, apparatus, process or mechanism for transferring data and/or text from one or more devices, computing systems, server systems, databases, web site/web resources and/or any devices having a data storage capability with one or more other devices, computing systems, server systems, databases, web site/web resources and/or any devices having a data storage capability, such as those described herein, known in the relevant art at the time of filing, or as developed thereafter.

In one embodiment, the data representing personal and/or family health information associated with a user is obtained by process for forecasting the consequences of healthcare utilization choices 200 at OBTAIN DATA REPRESENTING PERSONAL AND/OR FAMILY HEALTH INFORMATION ASSOCIATED WITH A USER OPERATION 203 from invoices/patient bills, claims data and/or healthcare coding data provided to process for forecasting the consequences of healthcare utilization choices 200 by healthcare providers such as, but not limited to: doctors; nurses; technicians; therapists; pharmacists; healthcare insurance providers; counselors; alternative medicine practitioners; medical facilities; doctor's offices; hospitals; emergency rooms; clinics; urgent care centers; alternative medicine clinics/facilities; dentist offices and/or physical therapy clinics/facilities.

In one embodiment, the data representing personal and/or family health information is obtained by process for forecasting the consequences of healthcare utilization choices from Explanation of Benefits (EOB) data as provided to process for forecasting the consequences of healthcare utilization choices 200 by one or more healthcare providers and/or by a user of process for forecasting the consequences of healthcare utilization choices 200 of FIG. 2. In one embodiment, the one or more healthcare provider(s) transfer electronic representations of the EOBs, typically in specific formats, to process for forecasting the consequences of healthcare utilization choices 200.

In one embodiment, the EOB data obtained by process for forecasting the consequences of healthcare utilization choices 200 of FIG. 2 includes healthcare coding data. The healthcare coding data is typically based on one or more standardized coding schemes such as the International Classification of Diseases (ICD), the Healthcare Common Procedure Coding System (HCPCS), the Current Procedural Terminology (CPT) and/or any other standardized healthcare coding data. In one embodiment, healthcare coding data and/or healthcare descriptions associated with the healthcare coding data and/or EOB data discussed above are used at least for generating a personalized disease predisposition profile for the user as is discussed below.

In one embodiment, the data representing personal and/or family health information associated with a user is provided to process for forecasting the consequences of healthcare utilization choices 200 at OBTAIN DATA REPRESENTING PERSONAL AND/OR FAMILY HEALTH INFORMATION ASSOCIATED WITH A USER OPERATION 203 by a user, or a user's agent, entering the data representing personal and/or family health information associated with a user into a user interface associated with a computing system, such as computing systems 100 or 150 of FIG. 1 as described above.

Returning to FIG. 2, in some embodiments, the data representing personal and/or family health information associated with a user is obtained by process for forecasting the consequences of healthcare utilization choices 200 at OBTAIN DATA REPRESENTING PERSONAL AND/OR FAMILY HEALTH INFORMATION ASSOCIATED WITH A USER OPERATION 203 using any means for obtaining, collecting, accessing, entering, transferring, relaying and/or providing data in any form, to a process, such as process for forecasting the consequences of healthcare utilization choices 200, such as those described herein, known in the relevant art at the time of filing, or as developed thereafter.

In one embodiment, once the data representing personal and/or family health information associated with a user is obtained at OBTAIN DATA REPRESENTING PERSONAL AND/OR FAMILY HEALTH INFORMATION ASSOCIATED WITH A USER OPERATION 203, process flow proceeds to GENERATE PERSONALIZED DISEASE PREDISPOSITION PROFILE FOR THE USER OPERATION 205. In one embodiment at GENERATE PERSONALIZED DISEASE PREDISPOSITION PROFILE FOR THE USER OPERATION 205, the data representing personal and/or family health information associated with a user is analyzed by process for forecasting the consequences of healthcare utilization choices 200.

In one embodiment, at GENERATE PERSONALIZED DISEASE PREDISPOSITION PROFILE FOR THE USER OPERATION 205 process for forecasting the consequences of healthcare utilization choices 200 analyzes the obtained demographic and actuarial data components of the data representing personal and/or family health information associated with a user and the data representing the user's generational cohort group to determine the user's predisposition to disease.

In addition, in one embodiment, at GENERATE PERSONALIZED DISEASE PREDISPOSITION PROFILE FOR THE USER OPERATION 205 process for forecasting the consequences of healthcare utilization choices 200 analyzes the obtained demographic and actuarial data components of the data representing personal and/or family health information associated with a user for the data representing the user's generational cohort group, which is then compared with the user's health and personal data components of the data representing personal and/or family health information associated with a user of OBTAIN DATA REPRESENTING PERSONAL AND/OR FAMILY HEALTH INFORMATION ASSOCIATED WITH A USER OPERATION 203 to determine any deviations between recommended healthcare appropriate for the user's generational cohort group and the user's actual historical healthcare utilization to generate a personalized disease predisposition profile for the user. In one embodiment, additional analyses are performed by process for forecasting the consequences of healthcare utilization choices 200 to determine potential disease risk factors from the user's health and personal data components of the data representing personal and/or family health information associated with a user.

For illustrative purposes, a simple example is provided below for one embodiment of process for forecasting the consequences of healthcare utilization choices 200. In one embodiment, process for forecasting the consequences of healthcare utilization choices 200 identifies at GENERATE PERSONALIZED DISEASE PREDISPOSITION PROFILE FOR THE USER OPERATION 205, healthcare coding data of ICD-10:I10 in a portion of the user health data component obtained at OBTAIN DATA REPRESENTING PERSONAL AND/OR FAMILY HEALTH INFORMATION ASSOCIATED WITH A USER OPERATION 203. ICD-10:I10 is a standardized healthcare code for hypertension (high blood pressure.) Using the health data component of the data representing personal and/or family health information associated with a user, process for forecasting the consequences of healthcare utilization choices 200 determines using ICD-10:I10, that the user is predisposed to coronary artery disease, heart attack, abnormal heartbeat, stroke, kidney failure, and eye damage.

In one embodiment, once the data representing personal and/or family health information associated with a user has been analyzed by process for forecasting the consequences of healthcare utilization choices 200 at GENERATE PERSONALIZED DISEASE PREDISPOSITION PROFILE FOR THE USER OPERATION 205, process flow proceeds to PERFORM HEALTHCARE UTILIZATION ANALYSIS OPERATION 207. In one embodiment, at PERFORM HEALTHCARE UTILIZATION ANALYSIS OPERATION 207, process for forecasting the consequences of healthcare utilization choices 200 analyzes the data representing a user's actual historical healthcare utilization information to develop metrics related to the user's current state of health based, at least in part, on all or part of comparisons with the user's generational cohort group. In one embodiment, the metrics are developed by process for forecasting the consequences of healthcare utilization choices 200 using one or more healthcare utilization models in conjunction with at least the demographic and actuarial data components of the data representing personal and/or family health information associated with a user of OBTAIN DATA REPRESENTING PERSONAL AND/OR FAMILY HEALTH INFORMATION ASSOCIATED WITH A USER OPERATION 203.

One of ordinary skill in the art will appreciate that the numerous methods, mechanisms, processes and procedures for developing one or more healthcare utilization models are possible and that mechanisms, processes and procedures for developing utilization models are known in the relevant art. Therefore, a more detailed discussion of specific methods, mechanisms, processes and procedures for developing one or more healthcare utilization models is omitted here for simplicity and clarity of disclosure.

In one embodiment, at PERFORM HEALTHCARE UTILIZATION ANALYSIS OPERATION 207 process for forecasting the consequences of healthcare utilization choices 200 uses one healthcare utilization model based on whether a user historically has received recommended healthcare and/or had sufficient healthcare insurance commensurate with the user's generational cohort group.

In one embodiment, if at PERFORM HEALTHCARE UTILIZATION ANALYSIS OPERATION 207 process for forecasting the consequences of healthcare utilization choices 200 determines that the user has historically received little or no recommended healthcare and/or has not had sufficient healthcare insurance commensurate with the user's generational cohort group, process for forecasting the consequences of healthcare utilization choices 200 employs a first model from the one or more healthcare utilization models that is based on the user receiving little or no recommended healthcare and/or having insufficient healthcare insurance. For example, in one embodiment, using the hypertensive state of health of the user discussed above, process for forecasting the consequences of healthcare utilization choices 200 would develop metrics which provide a less favorable healthcare forecast in terms of projected longevity, future quality of life/disability, cost/benefit of the user's choice, and/or future healthcare costs with respect to the portion of the user's generational cohort group having a similar hypertensive state of health but who received recommended healthcare.

Alternately, in one embodiment, if process for forecasting the consequences of healthcare utilization choices 200 determines that the user has historically received recommended healthcare and/or had sufficient healthcare insurance commensurate with the user's generational cohort group, process for forecasting the consequences of healthcare utilization choices 200 employs a second model from the one or more healthcare utilization models that is based on the user receiving recommended healthcare and/or sufficient healthcare insurance. For example, continuing with the hypertensive state of health of the user discussed above, process for forecasting the consequences of healthcare utilization choices 200 would develop metrics which provides a similar healthcare forecast in terms of projected longevity, future quality of life/disability, cost/benefit of the user's choice, and/or healthcare costs to the portion of the user's generational cohort group having a similar hypertensive state of health and who received the equivalent recommended healthcare.

In one embodiment, process for forecasting the consequences of healthcare utilization choices 200 uses a third model from the one or more healthcare utilization models for forecasting of future healthcare consequences based on the user's choice. For example, if the user indicates to process for forecasting the consequences of healthcare utilization choices 200, that he or she chooses to make recommended lifestyle changes and/or behavior modifications, process for forecasting the consequences of healthcare utilization choices 200 uses a more optimistic forecast model included in the one or more healthcare utilization models.

Continuing with the example hypertensive state of health of the user discussed above, process for forecasting the consequences of healthcare utilization choices 200 provides the user with a mitigation regimen for treating his or her hypertensive state, such as taking hypertension medication, getting at least 30 minutes of cardiovascular exercise per day, avoiding foods high in cholesterol, losing weight, taking a daily dose of aspirin, stopping smoking, getting regular healthcare checkups, and like recommendations obtained by process for process for forecasting the consequences of healthcare utilization choices from one or more healthcare providers.

In the above example, process for forecasting the consequences of healthcare utilization choices 200 would develop metrics which provide a similar healthcare forecast in terms of projected longevity, future quality of life/disability, cost/benefit of the user's choice, and/or future healthcare costs with the portion of the user's generational cohort group having a similar hypertensive state of health and who performed the recommended mitigating regimen. Alternately, if the user indicates to process for forecasting the consequences of healthcare utilization choices 200 that he or she chooses not to make some or all of the recommended lifestyle changes and/or behavior modifications, process for forecasting the consequences of healthcare utilization choices 200 uses a more pessimistic forecast model included in the one or more healthcare utilization models which is scaled according to which, if any, parts of the mitigation regimen the user indicates he or she will implement.

In the above model example, process for forecasting the consequences of healthcare utilization choices 200 would develop metrics which provide a less favorable healthcare forecast for the user in terms of projected longevity, quality of life/disability, cost/benefit and/or future healthcare costs in comparison with the user's generational cohort group who have a similar hypertensive state of health and who actually performed the recommended mitigating regimen.

In one embodiment, using the personalized disease predisposition profile for the user, the healthcare utilization analysis performed at PERFORM HEALTHCARE UTILIZATION ANALYSIS OPERATION 207 by process for forecasting the consequences of healthcare utilization choices 200 provides a forecast for the user in terms of projected quality of life/disability based on comparisons with the user's generational cohort group.

In one embodiment, using the personalized disease predisposition profile for the user of GENERATE PERSONALIZED DISEASE PREDISPOSITION PROFILE FOR THE USER OPERATION 205, the healthcare utilization analysis performed at PERFORM HEALTHCARE UTILIZATION ANALYSIS OPERATION 207 by process for forecasting the consequences of healthcare utilization choices 200 provides a forecast for the user in terms of projected longevity based on comparisons with the user's generational cohort group.

In one embodiment, using the personalized disease predisposition profile for the user of GENERATE PERSONALIZED DISEASE PREDISPOSITION PROFILE FOR THE USER OPERATION 205, the healthcare utilization analysis performed at PERFORM HEALTHCARE UTILIZATION ANALYSIS OPERATION 207 by process for forecasting the consequences of healthcare utilization choices 200 provides a forecast for the user in terms of projected future healthcare costs based on comparisons with the user's generational cohort group.

In one embodiment, once the healthcare utilization analysis at PERFORM HEALTHCARE UTILIZATION ANALYSIS OPERATION 207 of process for forecasting the consequences of healthcare utilization choices 200 has completed, process flow proceeds to GENERATE HEALTHCARE UTILIZATION CONSEQUENCES REPORT OPERATION 209.

In one embodiment, at GENERATE HEALTHCARE UTILIZATION CONSEQUENCES REPORT OPERATION 209 some or all of the results of the healthcare utilization analysis performed by process for forecasting the consequences of healthcare utilization choices 200 at PERFORM HEALTHCARE UTILIZATION ANALYSIS OPERATION 207 are collected in a healthcare utilization consequences report.

In one embodiment, the healthcare utilization consequences report generated by process for forecasting the consequences of healthcare utilization choices 200 at GENERATE HEALTHCARE UTILIZATION CONSEQUENCES REPORT OPERATION 209 includes comparative healthcare costs of one or more choices on the part of the user in terms of projected future healthcare costs. In one embodiment, the projected future healthcare costs is based, at least in part, on all, or part, of the actuarial and demographic data components of the data representing personal and/or family health information associated with a user of OBTAIN DATA REPRESENTING PERSONAL AND/OR FAMILY HEALTH INFORMATION ASSOCIATED WITH A USER OPERATION 203.

In one embodiment, the healthcare utilization consequences report generated at GENERATE HEALTHCARE UTILIZATION CONSEQUENCES REPORT OPERATION 209 by process for forecasting the consequences of healthcare utilization choices 200 includes the comparative healthcare costs of one or more choices on the part of the user in terms of projected longevity. In one embodiment, the projected longevity is based, at least in part, on all, or part of the actuarial and demographic data components of the data representing personal and/or family health information associated with the user of OBTAIN DATA REPRESENTING PERSONAL AND/OR FAMILY HEALTH INFORMATION ASSOCIATED WITH A USER OPERATION 203.

In one embodiment, the healthcare utilization consequences report generated at GENERATE HEALTHCARE UTILIZATION CONSEQUENCES REPORT OPERATION 209 by process for forecasting the consequences of healthcare utilization choices 200 includes the comparative costs of one or more choices on the part of the user in terms of projected quality of life/disability. In one embodiment, the projected quality of life/disability is based, at least in part, on all, or part, of the actuarial and demographic data components of the data representing personal and/or family health information associated with the user of OBTAIN DATA REPRESENTING PERSONAL AND/OR FAMILY HEALTH INFORMATION ASSOCIATED WITH A USER OPERATION 203.

In one embodiment, the healthcare utilization consequences report generated at GENERATE HEALTHCARE UTILIZATION CONSEQUENCES REPORT OPERATION 209 generated by process for forecasting the consequences of healthcare utilization choices 200 includes some or all of the results of the healthcare utilization analysis at PERFORM HEALTHCARE UTILIZATION ANALYSIS OPERATION 207 is determined using one or more healthcare utilization models of process for forecasting the consequences of healthcare utilization choices 200.

In one embodiment, once the healthcare utilization consequences report has been generated at GENERATE HEALTHCARE UTILIZATION CONSEQUENCES REPORT OPERATION 209, process flow proceeds to PROVIDE HEALTHCARE UTILIZATION CONSEQUENCES REPORT TO USER OPERATION 211. In one embodiment, the healthcare utilization consequences report generated by process for forecasting the consequences of healthcare utilization choices 200 at PROVIDE HEALTHCARE UTILIZATION CONSEQUENCES REPORT TO USER OPERATION 211, is provided to a user via a computing system, for example via computing system 100 or 150 of FIG. 1, and/or another computing system as described herein, known in the relevant art at the time of filing, or as developed thereafter.

In one embodiment, the healthcare utilization consequences report generated by process for forecasting the consequences of healthcare utilization choices 200 at GENERATE HEALTHCARE UTILIZATION CONSEQUENCES REPORT OPERATION 209, is provided to a user at PROVIDE HEALTHCARE UTILIZATION CONSEQUENCES REPORT TO USER OPERATION 211 via a computing system implemented data management system, such as computing system implemented data management system 180 of FIG. 1, or other computing systems such as those described herein, known in the relevant art at the time of filing, or as developed thereafter.

In one embodiment, the healthcare utilization consequences report generated by process for forecasting the consequences of healthcare utilization choices 200 at GENERATE HEALTHCARE UTILIZATION CONSEQUENCES REPORT OPERATION 209, is provided to the user at PROVIDE HEALTHCARE UTILIZATION CONSEQUENCES REPORT TO USER OPERATION 211 in an electronic format via a network, such as those described herein, known in the relevant art at the time of filing, or as developed thereafter.

In one embodiment, the healthcare utilization consequences report generated by process for forecasting the consequences of healthcare utilization choices 200 at GENERATE HEALTHCARE UTILIZATION CONSEQUENCES REPORT OPERATION 209, is provided to the user via any mechanism for transferring and/or relating information, such as those described herein, known in the relevant art at the time of filing, or as developed thereafter.

In one embodiment, a cost/benefit analysis based on receiving preventative healthcare and/or alternative healthcare treatment regimens is provided to a user by process for forecasting the consequences of healthcare utilization choices 200 at PROVIDE HEALTHCARE UTILIZATION CONSEQUENCES REPORT TO USER OPERATION 211.

For illustration purposes, an exemplary healthcare utilization consequences report is provided in Table 1 below. Table 1, illustrates how, in one embodiment, process for forecasting the consequences of healthcare utilization choices 200 allows the user to evaluate the consequences of various choices regarding his or her healthcare decision-making.

TABLE 1 exemplary healthcare utilization consequences report

Personal Information

Name.: John Smith Gender: Male
Age: 41 Height: 5'10'
Weight: 230 lbs RF: 7 [1-10]
Occupation: Air traffic controller SFO RF: 9 [1-10]
Marital Status: Divorced RF: 5 [1-10]
Address: 123 Boot Hill, CA 94105 RF: 3 [1-10]
Email: JSmith@doa.net
Phone: (415)867-5309
Weighted Personal Information RF: 6 [1-10]
Identified disease predisposition risk factors Genetic: Heart disease (maternal) RF: 7 [1-10]
Status: Deceased Age at Death: 63 RF: 7 [1-10]
Diet: POOR RF: 6 [1-10]
Smoker: Yes RF: 9 [1-10]

TABLE 1-continued exemplary healthcare utilization consequences report

Healthcare Utilization/Compliance: POOR RF: 8 [1-10]
Patient: Hypertension (Stage 1) RF:6 [1-10]
Weighted Health RF: 7 [1-10]
Weighted Cumulative Risk Factors Total RF Score: 7 [1-10]  HIGH RISK 
Recommendations Consult physician immediately for hypertension
medication; stop smoking; implement recommended lifestyle
changes; reducing weight, with a body mass index (BMI) of
18.5 to 24.9; reducing sodium in your diet to about 2.3 g
a day, exercising, such as brisk walking that raises your
heart rate for at least 30 minutes everyday, limit
alcoholic drinks to 2 drinks a day; get 3,500 mg of
potassium in the user's diet every day; and following the
Dietary Approaches to Stop Hypertension (DASH) eating
plan, a diet that is rich in fruits, vegetables, and low-
fat dairy products, with reduced amounts of saturated and
total fats.
Consequences Evaluation No Mitigation
Expected lifespan: 65 years
Complications: Reduced mobility; shortness of
breath; probable heart attack after age 50.
Quality of Life: Significantly impaired after age 60.
Economic Evaluation Healthcare costs expected to exceed generational cohort
group by 30% or $175,000 by age 65 without mitigation.
Comparison Information With Mitigation
Expected lifespan: 73 years
Healthcare costs expected to equal generational cohort
group of $122,500 by age 73 with mitigation.
Economic savings of $52,500 in today's dollars and an
expected increase in lifespan of 8 years.
Quality of Life: Slightly impaired after age 65.
Cost/Benefit: $175,000/$122,500.

Continuing with the hypertensive example shown in Table 1 above, the user, John Smith, is an air traffic controller at San Francisco International Airport. John's occupation is determined by process for forecasting the consequences of healthcare utilization choices 200 to be a very high stress occupation which carries a risk factor (RF) of 9 VERY HIGH on a scale of 1-10, with 10 being the highest risk.

Based on John's age of 41, height of 5'10" and weight of 230 lbs, process for forecasting the consequences of healthcare utilization choices 200 determined that John's weight represents a high risk and carries a RF of 7 HIGH.

John is also divorced, which based on statistics obtained by process for forecasting the consequences of healthcare utilization choices 200, indicates that divorced males are at a higher risk of developing diseases and carries a moderate RF of 5 MODERATE.

John lives on Boot Hill, a relatively affluent area of San Francisco. Boot Hill carries a low RF of 3 LOW, based on statistics obtained by process for forecasting the consequences of healthcare utilization choices 200 such as crime rates, environmental influences, age of home, and proximity to emergency healthcare resources.

The above personal information metrics are analyzed by process for forecasting the consequences of healthcare utilization choices 200 which assigns a weighted RF of 6 MODERATELY HIGH.

Turning to John's identified disease predisposition risk factors, process for forecasting the consequences of healthcare utilization choices 200 determines that John's mother died prematurely at age 63 due to complications arising out of heart disease. Based on this familial risk factor, process for forecasting the consequences of healthcare utilization choices 200 assigns a RF of 7 HIGH, indicating that heart disease has a genetic component, particularly when passed maternally.

As discussed above, John is hypertensive at a stage 1 level (140-159 mmHg or diastolic=90-99 mmHg considered mild hypertension,) which carries a RF of 6 MODERATELY HIGH.

Based on statistics obtained by process for forecasting the consequences of healthcare utilization choices 200, the health risk imposed by John's mild hypertension is increased due to his family history of heart disease. Additional health risks determined by process for forecasting the consequences of healthcare utilization choices 200 include John's poor diet RF of 6 MODERATELY HIGH; John's smoking habit RF of 9 VERY HIGH; John's lack of compliance with recommended healthcare when compared with John's generational cohort group carries a RF of 8 VERY HIGH. From these determinations, process for forecasting the consequences of healthcare utilization choices 200 determines a Weighted Health RF of 7 HIGH to John's identified predisposition disease risk factors and determines an overall RF based on John's personal information and identified predisposition disease of RF of 7 HIGH.

John's current state of health is considered to be at high risk of developing serious health problems within the next 10 years. To mitigate the development of the future state of health problems, process for forecasting the consequences of healthcare utilization choices 200 provides a recommended regimen. In addition, in one embodiment, the healthcare utilization consequences report provides the hard facts regarding John's current state of health based on choices made by John now. In this example, if John takes no action, John is statistically projected to live to age 65 and his projected quality of life/disability will be significantly impaired after age 60.

In addition, in one embodiment, John is projected to suffer a life threatening heart attack some time after age 50. Economically, John could expect a significant increase in healthcare costs of approximately 30% by age 65 assuming John chooses not to take any mitigating actions. However, if John chooses to take mitigating actions from this point forward, John is projected to live to approximately 73 years old, may only suffer limited impairment after age 65 and save approximately $52,500 in healthcare costs.

For example, in one embodiment, if John chooses to do nothing about his hypertension, John's healthcare costs are projected to be $175,000 over his determined actuarial lifetime of 65 years with a negative benefit of shortening the John's lifespan by 8 years and an increase in healthcare costs of $52,500 when compared to John's generational cohort group who actually implement the regimen.

Once process for forecasting the consequences of healthcare utilization choices 200 at PROVIDE HEALTHCARE UTILIZATION CONSEQUENCES REPORT TO USER OPERATION 211 has completed, process for forecasting the consequences of healthcare utilization choices 200 concludes at END OPERATION 213.

Figure 3:
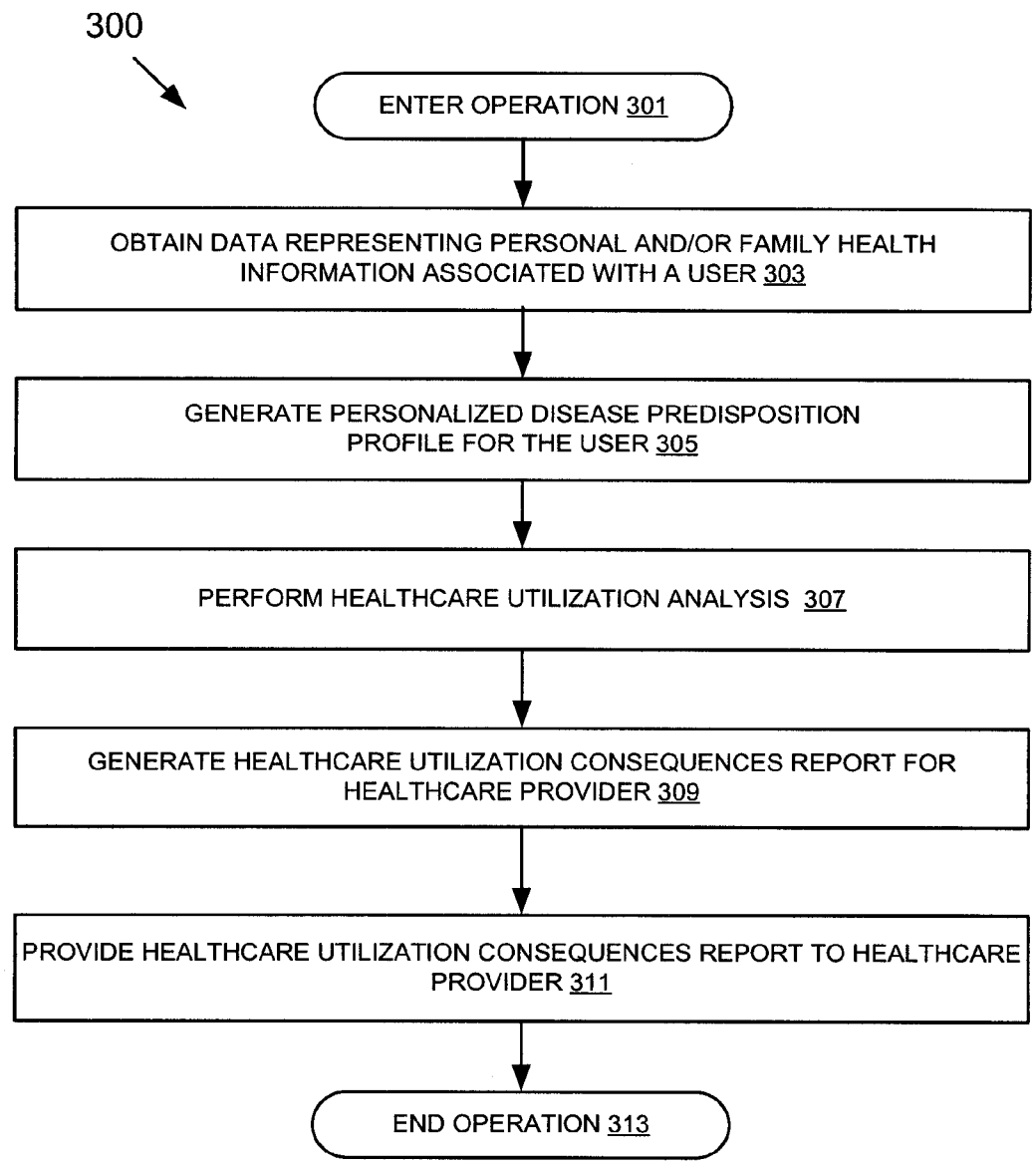
FIG. 3 is a flow chart for implementing a process for forecasting the consequences of healthcare utilization choices in accordance with one embodiment.

FIG. 3 is a flow chart depicting a process for forecasting the consequences of healthcare utilization choices 300 in accordance with one embodiment. In this embodiment, process flow of process for forecasting the consequences of healthcare utilization choices 300 is generally the same as previously described for process for forecasting the consequences of healthcare utilization choices 200 of FIG. 2. To minimize undue duplication and improve clarity, only those portions of process for forecasting the consequences of healthcare utilization choices 300 which may differ from process for forecasting the consequences of healthcare utilization choices 200 of FIG. 2 are discussed below.

In one embodiment, the healthcare utilization consequences report generated by process for forecasting the consequences of healthcare utilization choices 300 at GENERATE HEALTHCARE UTILIZATION CONSEQUENCES REPORT FOR HEALTHCARE PROVIDER OPERATION 309, is generated as discussed with respect at GENERATE HEALTHCARE UTILIZATION CONSEQUENCES REPORT OPERATION 209 (FIG. 2), however, the level of detail and/or the type of information collected in the generated healthcare utilization consequences report may be customized to provide a more focused marketing opportunity for a healthcare provider as is discussed below. In one embodiment, once the healthcare utilization consequences report has been generated at GENERATE HEALTHCARE UTILIZATION CONSEQUENCES REPORT FOR HEALTHCARE PROVIDER OPERATION 309, process flow proceeds to PROVIDE HEALTHCARE UTILIZATION CONSEQUENCES REPORT TO HEALTHCARE PROVIDER OPERATION 311. In this embodiment, the generated healthcare utilization consequences report of GENERATE HEALTHCARE UTILIZATION CONSEQUENCES REPORT FOR HEALTHCARE PROVIDER OPERATION 309 is provided in an electronic format and/or by hardcopy at PROVIDE HEALTHCARE UTILIZATION CONSEQUENCES REPORT TO HEALTHCARE PROVIDER OPERATION 311.

In one example, in one embodiment, continuing with the hypertension example for John Smith discussed above, the generated healthcare utilization consequences report of GENERATE HEALTHCARE UTILIZATION CONSEQUENCES REPORT FOR HEALTHCARE PROVIDER OPERATION 309, may provide John's contact information along with the recommendation for John to visit a physician immediately to a list of physicians who specialize in hypertension. In one embodiment, the generated healthcare utilization consequences report may be provided to those physicians within a predetermined distance to John's home on Boot Hill at PROVIDE HEALTHCARE UTILIZATION CONSEQUENCES REPORT TO HEALTHCARE PROVIDER OPERATION 311.

In another example, in one embodiment, the healthcare utilization consequences report of GENERATE HEALTHCARE UTILIZATION CONSEQUENCES REPORT FOR HEALTHCARE PROVIDER OPERATION 309 may include John's contact information and the recommendation for John to receive hypertension medications which is then provided to one or more pharmaceutical companies at PROVIDE HEALTHCARE UTILIZATION CONSEQUENCES REPORT TO HEALTHCARE PROVIDER OPERATION 311. In one embodiment, one or more of the pharmaceutical companies provide John with pharmaceutical information and/or discount coupons for trial of their hypertension medication(s).

In another example, in one embodiment, the healthcare utilization consequences report of GENERATE HEALTHCARE UTILIZATION CONSEQUENCES REPORT FOR HEALTHCARE PROVIDER OPERATION 309 may include John's contact information and the recommendation for John to perform 30 minutes of exercise per day which is then provided to one or more health clubs at PROVIDE HEALTHCARE UTILIZATION CONSEQUENCES REPORT TO HEALTHCARE PROVIDER OPERATION 311. In one embodiment, the one or more health clubs providers provide John with promotional offers related to their health clubs. In one embodiment, the generated healthcare utilization consequences report may be provided to those health clubs within a predetermined distance to John's home on Boot Hill.

In another example, in one embodiment, the healthcare utilization consequences report of GENERATE HEALTHCARE UTILIZATION CONSEQUENCES REPORT FOR HEALTHCARE PROVIDER OPERATION 309 may include John's contact information and the recommendation for John to lose weight which is then provided to one or more weight management providers at PROVIDE HEALTHCARE UTILIZATION CONSEQUENCES REPORT TO HEALTHCARE PROVIDER OPERATION 311. In one embodiment, the one or more weight management providers provide John with promotional offers related to their weight management programs. In one embodiment, the generated healthcare utilization consequences report may be provided to those weight management providers within a predetermined distance to John's home on Boot Hill.

In another example, in one embodiment, the healthcare utilization consequences report of GENERATE HEALTHCARE UTILIZATION CONSEQUENCES REPORT FOR HEALTHCARE PROVIDER OPERATION 309 may include John's contact information and John's hypertension risk factor which is then provided to one or more healthcare facilities within a predetermined distance to John's home on Boot Hill at PROVIDE HEALTHCARE UTILIZATION CONSEQUENCES REPORT TO HEALTHCARE PROVIDER OPERATION 311.

In another example, in one embodiment, the healthcare utilization consequences report of GENERATE HEALTHCARE UTILIZATION CONSEQUENCES REPORT FOR HEALTHCARE PROVIDER OPERATION 309 may include John's contact information and John's hypertension risk factor which is then provided to one or more alternative healthcare providers at PROVIDE HEALTHCARE UTILIZATION CONSEQUENCES REPORT TO HEALTHCARE PROVIDER OPERATION 311. One or more of the alternative healthcare providers in this embodiment may then provide John with alternative mitigation regimens to treat his hypertension. In one embodiment, the generated healthcare utilization consequences report may be provided to those alternative healthcare providers within a predetermined distance to John's home on Boot Hill.

In one embodiment, once process for process for forecasting the consequences of healthcare utilization choices 300 completes at COMPARATIVE TREATMENTS REPORT TO HEALTHCARE PROVIDERS 311, process for forecasting the consequences of healthcare utilization choices 300 concludes at END OPERATION 313.

Using processes for forecasting the consequences of healthcare utilization choices 200 and/or 300 (FIGS. 2 and 3), a user can evaluate the outcomes of various choices regarding receiving preventative healthcare and/or obtaining healthcare insurance in terms of projected economic, longevity and quality of life costs. Consequently, using processes for forecasting the consequences of healthcare utilization choices 200 and/or 300 (FIGS. 2,3), the user is more likely to make informed decisions regarding receiving preventative healthcare and/or obtaining healthcare insurance.

The present embodiments have been described in particular detail with respect to possible embodiments. Those of ordinary skill in the art will appreciate that the various disclosed embodiments may be practiced in other embodiments. For instance, those of ordinary skill in the art will appreciate that the order of operations discussed above was presented for illustrative purposes only and that other orders of operations, and combination of operations, are possible. Consequently, the order of operations discussed above does not limit the scope of the various inventive embodiments as claimed.

In addition, the nomenclature used for components, capitalization of component designations and terms, attributes, data structures, or any other programming or structural aspect is not significant, mandatory, or limiting, and the mechanisms that implement the embodiments or its features can have various different names, formats, and/or protocols. Further, the system and/or functionality of the embodiments may be implemented via various combinations of software and hardware, as described, or entirely in hardware elements. Also, particular divisions of functionality between the various components described herein are merely exemplary, and not mandatory or significant. Consequently, functions performed by a single component may, in some embodiments, be performed by multiple components, and functions performed by multiple components may, in some embodiments, be performed by a single component.

Some portions of the above description present the features of the embodiments in terms of algorithms and symbolic representations of operations, or algorithm-like representations, of operations on information/data. These algorithmic and/or algorithm-like descriptions and representations are the means used by those of ordinary skill in the art to most effectively and efficiently convey the substance of their work to others of ordinary skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "establishing," "defining," "sending," "receiving," "transmitting," "analyzing," "providing," "obtaining," "requesting," "accessing," "performing," "generating," "selecting," "listing," "determining," "storing," etc., refer to the action and processes of a computing system or similar electronic device that manipulates and operates on data represented as physical (electronic) quantities within the computing system memories, registers, caches or other information storage, transmission or display devices.

Certain aspects of the embodiments include process steps or operations and instructions described herein in an algorithmic and/or algorithmic-like form. It should be noted that the process steps and/or operations and instructions of the embodiments can be embodied in software, firmware, and/or hardware, and when embodied in software, can be downloaded to reside on and be operated from different platforms used by real time network operating systems.

The various embodiments also relate to an apparatus or system for performing the operations described herein. This apparatus or system may be specifically constructed for the required purposes, or the apparatus or system can comprise a general purpose system selectively activated or configured/reconfigured by a computer program stored on a computer program product as described herein that can be accessed by a computing system or other device.

Those of ordinary skill in the art will appreciate that the algorithms and operations presented herein are not inherently related to any particular computing system, computer architecture, computer or industry standard, or any other specific apparatus. Various general purpose systems may also be used with programs in accordance with the teachings herein, or it may prove more convenient/efficient to construct more specialized apparatuses to perform the required operations described herein.

The required structure for a variety of these systems will be apparent to those of ordinary skill in the art, along with equivalent variations. In addition, the embodiments are not described with reference to any particular programming language and it is appreciated that a variety of programming languages may be used to implement the teachings of the embodiments as described herein, and any references to a specific language or languages are provided for illustrative purposes only and for enablement of the contemplated best mode of the embodiments at the time of filing.

The various embodiments are also well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the subject matter. Accordingly, the disclosure of the various embodiments herein is intended to be illustrative, but not limiting, of the scope of the embodiments, which is set forth in the claims below.

In the discussion above, certain aspects of one embodiment include process steps and/or operations and/or instructions described herein for illustrative purposes in a particular order and/or grouping. However, the particular order and/or grouping shown and discussed herein is illustrative only and not limiting. Those of ordinary skill in the art will appreciate that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein does not limit the scope of the invention as claimed below.

In addition, the operations shown in the figures are identified using a particular nomenclature for ease of description and understanding, but other nomenclature is often used in the art to identify equivalent operations.

Therefore, numerous variations, whether explicitly provided for by the specification or implied by the specification or not, may be implemented by one of ordinary skill in the art in view of this disclosure.

What is claimed:

1. A system for forecasting the consequences of healthcare utilization choices comprising:
    a processor; and
    a memory coupled to the processor, the memory having stored therein instructions which when executed by the processor perform a process for forecasting the consequences of healthcare utilization choices comprising:
        obtaining electronic data representing personal and family health information associated with a user, the data being obtained over a network from at least one healthcare provider, the data comprising any historical and present user illnesses, user injuries, user surgeries, user's actual healthcare utilization, healthcare insurance coverage utilized by the user, medications taken by the user, familial genetic disorders, and compliance with recommended healthcare routines, regimens, programs and medications;
        generating a personalized disease predisposition profile based at least in part on the obtained data representing personal and family health information associated with a user, the personalized disease predisposition profile comprising a determination of the user's predisposition to disease, and risk factors the user has to particular diseases;
        performing a healthcare utilization analysis using the generated personalized disease predisposition profile;
        generating a healthcare utilization consequences report based at least in part on results obtained from the healthcare utilization analysis, the healthcare utilization consequences report indicating one or more recommended lifestyle changes or behavior changes, a projected longevity, and an estimated future quality of life;
        providing the healthcare utilization consequences report to the user;
        receiving input from the user indicating one or more of the recommended lifestyle changes or behavior changes the user intends to implement, the system being operative to recommend exercise for at least a minimum number of minutes per day, taking particular medication, avoiding high cholesterol foods, losing weight, taking a daily dose of aspirin, and quitting smoking, based on whether the particular recommendation is appropriate according to the healthcare utilization analysis; and
        updating the healthcare utilization consequences report according to a model which accommodates the one or more recommended lifestyle changes or behavior changes the user intends to implement, the system being operable to update the healthcare utilization consequences report indicating any changes in projected longevity, any changes in the estimates future quality of life, and any cost/benefit of implementing the one or more recommended lifestyle or behavior changes.

2. The system for forecasting the consequences of healthcare utilization choices of claim 1, wherein the healthcare utilization consequences report is provided to a user in an electronic format.

3. The system for forecasting the consequences of healthcare utilization choices of claim 1, wherein data representing personal and family health information associated with a user comprises user health data, familial health data, user personal data, demographic data and actuarial data.

4. The system for forecasting the consequences of healthcare utilization choices of claim 1, wherein the healthcare utilization consequences report includes identified disease predisposition risk factors.

5. The system for forecasting the consequences of healthcare utilization choices of claim 4, wherein the healthcare utilization consequences report includes healthcare recommendations based at least in part on the identified disease predisposition risk factors.

6. The system for forecasting the consequences of healthcare utilization choices of claim 5, wherein the healthcare utilization consequences report includes a consequence evaluation based at least in part on the user's compliance with the healthcare recommendations.

7. The system for forecasting the consequences of healthcare utilization choices of claim 5, wherein the healthcare utilization consequences report includes an economic evaluation based at least in part on the user's compliance with the healthcare recommendations.

8. The system for forecasting the consequences of healthcare utilization choices of claim 1, wherein the obtained data representing personal and family health information associated with a user is specific to the user.

9. The system for forecasting the consequences of healthcare utilization choices of claim 1, wherein the user is a healthcare provider authorized to receive the healthcare utilization consequences report.

10. The system for forecasting the consequences of healthcare utilization choices of claim 9, wherein the authorized healthcare provider obtains specific target marketing information from the healthcare utilization consequences report.

11. A system for forecasting the consequences of healthcare utilization choices comprising:
   a computing system implemented data management system; and,
   a processor for executing a process for forecasting the consequences of healthcare utilization choices, the process for forecasting the consequences of healthcare utilization choices comprising:
   obtaining electronic data representing personal and family health information associated with a user, the data being obtained over a network from at least one healthcare provider, the data comprising any historical and present user illnesses, user injuries, user surgeries, user's actual healthcare utilization, healthcare insurance coverage utilized by the user, medications taken by the user, familial genetic disorders, and compliance with recommended healthcare routines, regimens, programs and medications;
   generating a personalized disease predisposition profile based at least in part on the obtained data representing personal and family health information associated with a user, the personalized disease predisposition profile comprising a determination of the user's predisposition to disease, and risk factors the user has to particular diseases;
   performing a healthcare utilization analysis using the generated personalized disease predisposition profile;
   generating a healthcare utilization consequences report based at least in part on results obtained from the healthcare utilization analysis, the healthcare utilization consequences report indicating one or more recommended lifestyle changes or behavior changes, a projected longevity, and an estimated future quality of life;
   providing the healthcare utilization consequences report to the user;
   receiving input from the user indicating one or more of the recommended lifestyle changes or behavior changes the user intends to implement, the system being operative to recommend exercise for at least a minimum number of minutes per day, taking particular medication, avoiding high cholesterol foods, losing weight, taking a daily dose of aspirin, and quitting smoking, based on whether the particular recommendation is appropriate according to the healthcare utilization analysis; and
   updating the healthcare utilization consequences report according to a model which accommodates the one or more recommended lifestyle changes or behavior changes the user intends to implement, the system being operable to update the healthcare utilization consequences report indicating any changes in projected longevity, any changes in the estimates future quality of life, and any cost/benefit of implementing the one or more recommended lifestyle or behavior changes.

12. The system for forecasting the consequences of healthcare utilization choices of claim 11, wherein the healthcare utilization consequences report is provided to the user in an electronic format.

13. The system for forecasting the consequences of healthcare utilization choices of claim 11, wherein data representing personal and family health information associated with a user is selected from the group consisting of user health data, familial health data, user personal data, demographic data and actuarial data.

14. The system for forecasting the consequences of healthcare utilization choices of claim 11, wherein the healthcare utilization consequences report includes identified disease predisposition risk factors.

15. The system for forecasting the consequences of healthcare utilization choices of claim 14, wherein the healthcare utilization consequences report includes healthcare recommendations based at least in part on the identified disease predisposition risk factors.

16. The system for forecasting the consequences of healthcare utilization choices of claim 15, wherein the healthcare utilization consequences report includes a consequence evaluation based at least in part on the user's compliance with the healthcare recommendations.

17. The system for forecasting the consequences of healthcare utilization choices of claim 15, wherein the healthcare utilization consequences report includes an economic evaluation based at least in part on the user's compliance with the healthcare recommendations.

18. The system for forecasting the consequences of healthcare utilization choices of claim 11, wherein the obtained data representing personal and family health information associated with a user is specific to the user.

19. The system for forecasting the consequences of healthcare utilization choices of claim 11, wherein the user is a healthcare provider authorized to receive the healthcare utilization consequences report.

20. The system for forecasting the consequences of healthcare utilization choices of claim 19, wherein the authorized healthcare provider obtains specific target marketing information from the healthcare utilization consequences report.

21. A computer program product for forecasting the consequences of healthcare utilization choices comprising:
   a nontransitory computer readable medium; and,
   a computer program code, encoded on the computer readable medium, comprising computer readable instructions for:
   obtaining electronic data representing personal and family health information associated with a user, the data being obtained over a network from at least one healthcare provider, the data comprising any historical and present user illnesses, user injuries, user surgeries, user's actual healthcare utilization, healthcare insurance coverage utilized by the user, medications taken by the user, familial genetic disorders, and compliance with recommended healthcare routines, regimens, programs and medications;
   generating a personalized disease predisposition profile based at least in part on the obtained data representing personal and family health information associated with a user, the personalized disease predisposition profile comprising a determination of the user's predisposition to disease, and risk factors the user has to particular diseases;

performing a healthcare utilization analysis using the generated personalized disease predisposition profile;

generating a healthcare utilization consequences report based at least in part on results obtained from the healthcare utilization analysis, the healthcare utilization consequences report indicating one or more recommended lifestyle changes or behavior changes, a projected longevity, and an estimated future quality of life;

providing the healthcare utilization consequences report to the user;

receiving input from the user indicating one or more of the recommended lifestyle changes or behavior changes the user intends to implement, the system being operative to recommend exercise for at least a minimum number of minutes per day, taking particular medication, avoiding high cholesterol foods, losing weight, taking a daily dose of aspirin, and quitting smoking, based on whether the particular recommendation is appropriate according to the healthcare utilization analysis; and updating the healthcare utilization consequences report according to a model which accommodates the one or more recommended lifestyle changes or behavior changes the user intends to implement, the system being operable to update the healthcare utilization consequences report indicating any changes in projected longevity, any changes in the estimates future quality of life, and any cost/benefit of implementing the one or more recommended lifestyle or behavior changes.

22. The computer program product for forecasting the consequences of healthcare utilization choices of claim 21, wherein data representing personal and family health information associated with a user is selected from the group consisting of user health data, familial health data, user personal data, demographic data and actuarial data.

23. The computer program product for forecasting the consequences of healthcare utilization choices of claim 21, wherein the healthcare utilization consequences report includes identified disease predisposition risk factors.

24. The computer program product for forecasting the consequences of healthcare utilization choices of claim 23, wherein the healthcare utilization consequences report includes healthcare recommendations based at least in part on the identified disease predisposition risk factors.

25. The computer program product for forecasting the consequences of healthcare utilization choices of claim 24, wherein the healthcare utilization consequences report includes an economic evaluation based at least in part on the user's compliance with the healthcare recommendations.

* * * * *

UNITED STATES PATENT AND TRADEMARK OFFICE
CERTIFICATE OF CORRECTION

| | | |
|---|---|---|
| PATENT NO. | : 8,041,580 B1 | Page 1 of 1 |
| APPLICATION NO. | : 12/039131 | |
| DATED | : October 18, 2011 | |
| INVENTOR(S) | : Steven Sholtis et al. | |

It is certified that error appears in the above-identified patent and that said Letters Patent is hereby corrected as shown below:

In the Claims

In Column 26, Line 38, Claim 1, replace "estimates" with --estimated--;
In Column 27, Line 67, Claim 11, replace "estimates" with --estimated--; and
In Column 30, Line 1, Claim 21, replace "estimates" with --estimated--.

Signed and Sealed this
Twenty-ninth Day of October, 2013

Teresa Stanek Rea
*Deputy Director of the United States Patent and Trademark Office*